(12) United States Patent
Kang et al.

(10) Patent No.: US 11,278,276 B2
(45) Date of Patent: Mar. 22, 2022

(54) MEDICAL THREAD INSERTION INSTRUMENT

(71) Applicant: OV MEDI CO., LTD., Gunpo-si (KR)

(72) Inventors: Yun Gyu Kang, Yongin-si (KR); Geung Gyu Gang, Seoul (KR)

(73) Assignee: OV MEDI Co., Ltd., Gunpo-si (KR)

( * ) Notice: Subject to any disclaimer, the term of this patent is extended or adjusted under 35 U.S.C. 154(b) by 7 days.

(21) Appl. No.: 16/763,654

(22) PCT Filed: Oct. 17, 2018

(86) PCT No.: PCT/KR2018/012215
§ 371 (c)(1),
(2) Date: May 13, 2020

(87) PCT Pub. No.: WO2019/139230
PCT Pub. Date: Jul. 18, 2019

(65) Prior Publication Data
US 2020/0275924 A1    Sep. 3, 2020

(30) Foreign Application Priority Data

Jan. 11, 2018    (KR) .................... 10-2018-0003809

(51) Int. Cl.
*A61B 17/06* (2006.01)
(52) U.S. Cl.
CPC .......... *A61B 17/06166* (2013.01); *A61B 2017/06176* (2013.01)
(58) Field of Classification Search
CPC ........... A61B 2017/06176; A61B 2017/06052; A61B 17/06166; A61B 17/06004; A61B 2017/00792; A61B 2017/06185; A61B 2017/0618; A61B 17/3468
See application file for complete search history.

(56) References Cited

U.S. PATENT DOCUMENTS

2013/0238021 A1*  9/2013  Gross ............... A61B 17/06166
                                                    606/228
2016/0278770 A1*  9/2016  Rustamova ...... A61B 17/06166

FOREIGN PATENT DOCUMENTS

| EP | 2671516 A1 * | 12/2013 | ....... A61B 17/06166 |
|---|---|---|---|
| KR | 10-2013-0010734 A | 1/2013 | |
| KR | 10-2014-0039600 A | 4/2014 | |
| KR | 10-1439228 B1 | 10/2014 | |
| KR | 10-1454659 B1 | 10/2014 | |
| KR | 10-2015-0107292 A | 9/2015 | |

OTHER PUBLICATIONS

International Search Report for PCT/KR2018/012215 dated Jan. 21, 2019 from Korean Intellectual Property Office.

* cited by examiner

*Primary Examiner* — Majid Jamialahmadi
(74) *Attorney, Agent, or Firm* — Paratus Law Group, PLLC

(57) ABSTRACT

Disclosed is a medical thread insertion instrument including: a medical thread having an outer surface thereof on which barbs are formed; a needle part having a cavity therein so that the medical thread is able to be inserted, the needle part including a needle having a predetermined length (L1); and a tube part having a cavity therein so that the needle is able to be inserted, the tube part being inserted into an inner side of the skin and including a tube having a length (L2) shorter than the length (L1) of the needle.

4 Claims, 10 Drawing Sheets

FIG. 5A FIG. 5B FIG. 5C
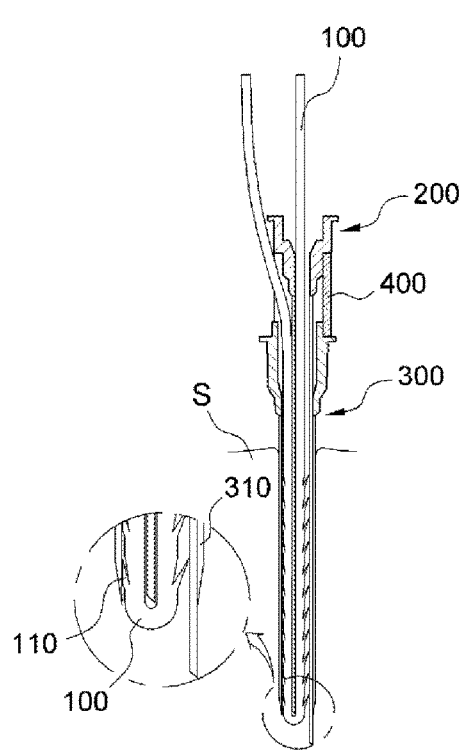
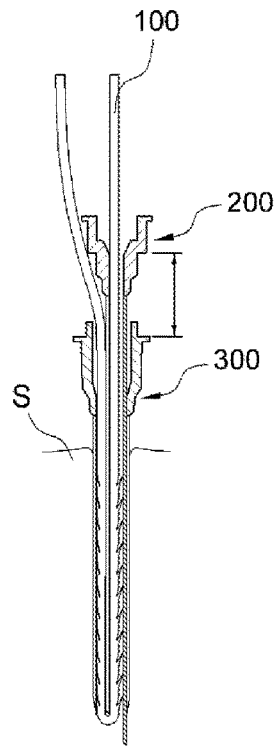
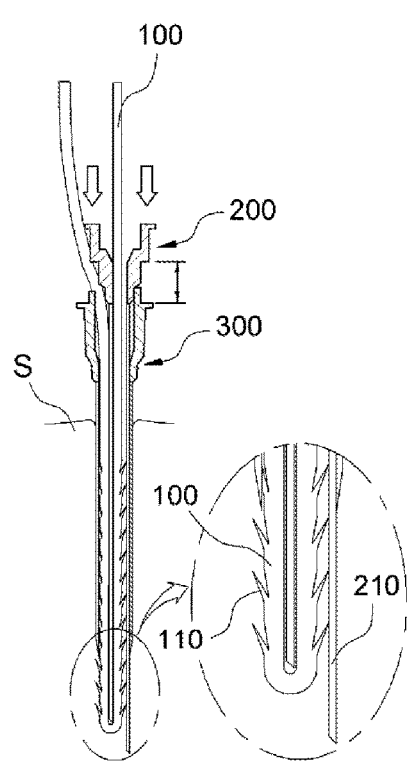

MEDICAL THREAD INSERTION INSTRUMENT

CROSS-REFERENCE TO PRIOR APPLICATIONS

This application is a National Stage Patent Application of PCT International Patent Application No. PCT/KR2018/012215 (filed on Oct. 17, 2018) under 35 U.S.C. § 371, which claims priority to Korean Patent Application No. 10-2018-0003809 (filed on Jan. 11, 2018), which are all hereby incorporated by reference in their entirety.

BACKGROUND

The present invention relates to a medical thread insertion instrument capable of easily inserting a medical thread into a human body and, more particularly, relates to a medical thread insertion instrument and a medical thread insertion method using the same, wherein the instrument guides an insertion of the medical thread so as to smoothly insert the medical thread into a skin tissue of the human body; may minimize the risk of side effects by pulling the medical thread out of the skin tissue even in the case where the insertion instrument is removed; and may inject bio injectable material between the skin tissue and the medical thread in order to provide smooth recovery of damaged skin tissue due to the insertion of the insertion instrument.

In general, a medical thread has been used to suture an incised surgical site after performing a surgery. When a wound is healed after suturing, it is necessary to perform a treatment to remove the used thread from the skin, and this treatment causes discomfort to a patient.

With the development of medical technology, time for suturing a surgical site is shortened, and when the surgical site is recovered after a certain time, the used medical thread is naturally biodegraded, and thus a separate treatment for removing the medical tread becomes unnecessary.

In addition, aside from the surgical suture, as the medical thread is inserted into wrinkled skin of the face, neck, arms, and the like to pull and fix the wrinkled skin, a treatment method using the medical thread to remove wrinkles of the skin is in spotlight. Furthermore, the medical thread is also used for a treatment of spinal pain, and arthritis of the knees and the like, that is, for strengthening of muscles around the joints.

Being used in these treatment methods, the medical thread is provided with an outer side surface of the central strand thereof on which barbs are protrudingly formed. When pulling a medical thread inserted into the skin tissue, these barbs make the pulling of the skin tissue easy. In order to facilitate the pulling of the skin tissue and to maintain the pull for a long time, the technology of the medical thread is gradually increasing in such a way that protruding directions of the barbs are arranged in different directions, or positions and intervals where barbs are formed are changed.

The medical thread may be contaminated by foreign substances or the like due to the fact that the medical thread required for treatment is exposed to outside for a long time, or due to a process in which the medical thread is pulled out after being inserted into the skin. Because of the contaminated medical thread, there is a problem in that the skin tissue is damaged, whereby the treated site becomes swollen and recovery takes a long period of time.

In addition, when a medical specialist mistakenly performs a treatment on an undesired site, a case occurs where the inserted medical thread is to be removed, and the shape of the barb of the medical thread causes damage such as tearing of the skin tissue.

SUMMARY

The present invention has been devised to solve the above problems, and the objective of the present invention is to provide a medical thread insertion instrument that may maximally reduce damage to the skin tissue when the medical thread is inserted into the skin, and may not cause any side effects even when the insertion instrument is pulled out of the skin when a position of the treatment site is needed to be changed.

In addition, the purpose of the present invention is to prevent breakage of the protrusions formed on the surface of the medical thread by maximally reducing contact with the skin tissue when the medical thread is inserted into the skin tissue, and is to maximally reduce occurrence of side effects caused by treatment by improving the supporting force that fixes the skin tissue and the medical thread to each other.

The present invention includes: a medical thread 100 having an outer surface thereof on which barbs 110 are formed; a needle part 200 having a cavity therein so that the medical thread 100 is able to be inserted, the needle part including a needle 210 having a predetermined length L1; and a tube part 300 having a cavity therein so that the needle 210 is able to be inserted, the tube part being inserted into an inner side of the skin and including a tube 310 having a length L2 shorter than the length L1 of the needle, wherein, when the tube part 300 into which the needle part 200 in which the medical thread 100 is embedded is inserted is inserted into a skin tissue S, as the needle 210 is inserted into the skin tissue S, an end part of the needle 210 is able to be protruded toward an outer side of the tube 310 due to a difference in length between the tube 310 and the needle 210.

In the present invention, a part of the medical thread 100 on which the barbs 110 are formed may be exposed to the skin tissue S toward an outer side of the end part of the protruding needle 210.

The present invention may further include a connection part 400 for maintaining an interval between the needle 210 and the tube 310, wherein the connection part 400 may be removed after the tube part 300 into which the needle part 200 in which the medical thread 100 is embedded is inserted is inserted.

In the present invention, an inner diameter d2 of a distal end part of the tube 310 through which a distal end part of the needle 210 is pulled out may be shorter than a length of the outer diameter D of the needle 310.

In the present invention, the needle part 200 may further include a needle guider 220 connected to an end of the needle 210 and having a groove or a protrusion 230 formed on an outer circumferential surface thereof in a longitudinal direction; and the tube part 300 may further include a tube guider 320 connected to an end of the tube 310 and having a protrusion or a groove 330 formed on an inner circumferential surface thereof in a longitudinal direction to correspond to the groove or the protrusion 230 of the needle guider, thus receiving the groove or the protrusion 230 of the needle guider 220 therein.

In the present invention, a rapid treatment may be performed by inserting a needle having a medical thread embedded therein and a tube simultaneously into the skin tissue. When being inserted into the skin tissue, the medical thread is not allowed to directly contact with the skin tissue, so as to prevent the barbs on the medical thread from being damaged when the medical thread is necessary to be corrected due to an incorrect insertion. In addition, the medical thread is prevented from being contaminated by being exposed to the outside.

In addition, the present invention may improve an engraftment rate between the medical thread and the skin tissue by injecting a biomaterial into the tube to penetrate the biomaterial into the skin tissue.

BRIEF DESCRIPTION OF THE DRAWINGS

FIGS. 5A to 5C are conceptual diagrams showing a sequence of insertion of the medical thread by using the medical thread insertion instrument of the present invention.

DETAILED DESCRIPTION

Hereinafter, exemplary embodiments of the medical thread insertion instrument of the present invention will be described in detail with reference to the drawings.

Figure 1:
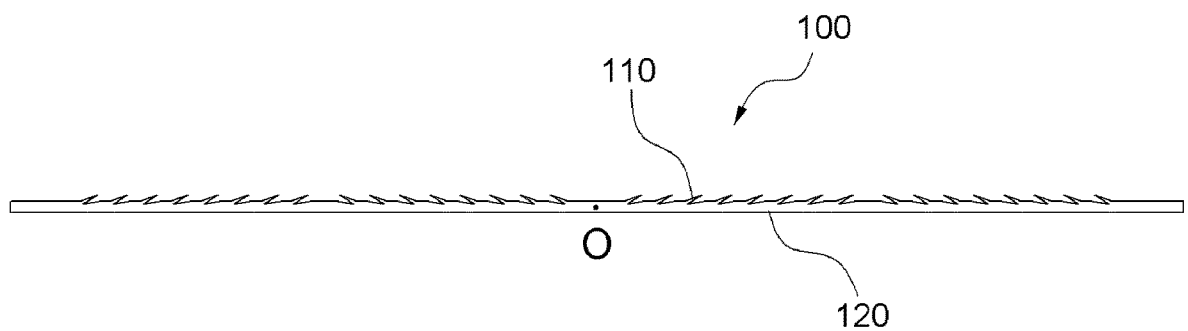
FIG. 1 is a conceptual diagram for a medical thread according to the present invention.
Figure 2:
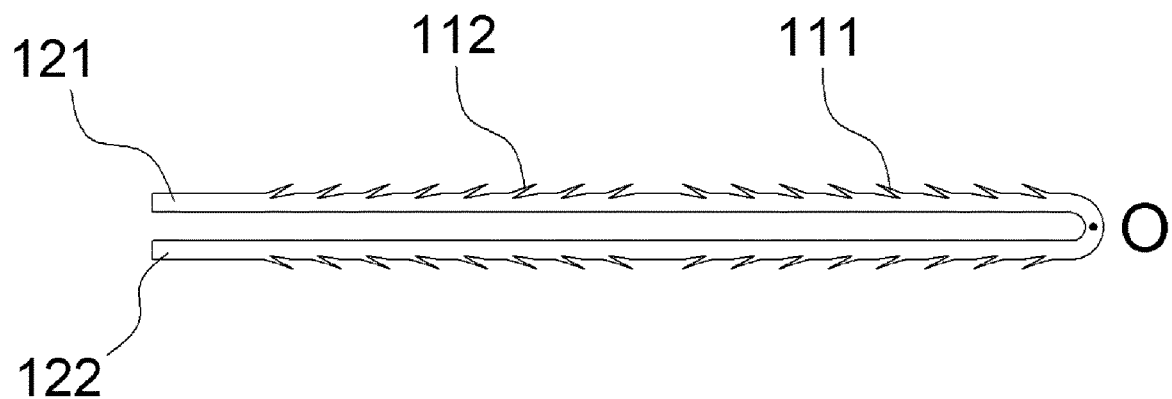
FIG. 2 is another conceptual diagram for the medical thread according to the present invention.

Referring to FIGS. 1 and 2, centering on a stem 120 thereof, a medical thread 100 is provided with the outer circumferential surface thereof having at least one barb 110 protrudingly formed thereon. The barb 110 is formed to be inclined while forming a predetermined angle in the longitudinal direction of the stem. It is preferable that the barbs 110 are symmetrically formed to the left and right sides with respect to the center O. Referring to FIG. 2, it is preferable that the barbs 110 have consistent directions when the medical thread is folded in half with respect to the center O. As shown in FIGS. 1 and 2, the barbs 110 may be formed in different directions. As shown in FIGS. 1 and 2, the directions of the barbs 110 are formed to be opposite to each other to lift the skin in the direction where pulling force acts by the barbs 111 protruding in either direction when gripping and pulling the ends 121 and 122 during the treatment process. When the pulling is stopped, the skin may be lifted in the opposite direction to a direction in which the pulling force is applied by the barbs 112 protruding in the other direction.

Figure 3:
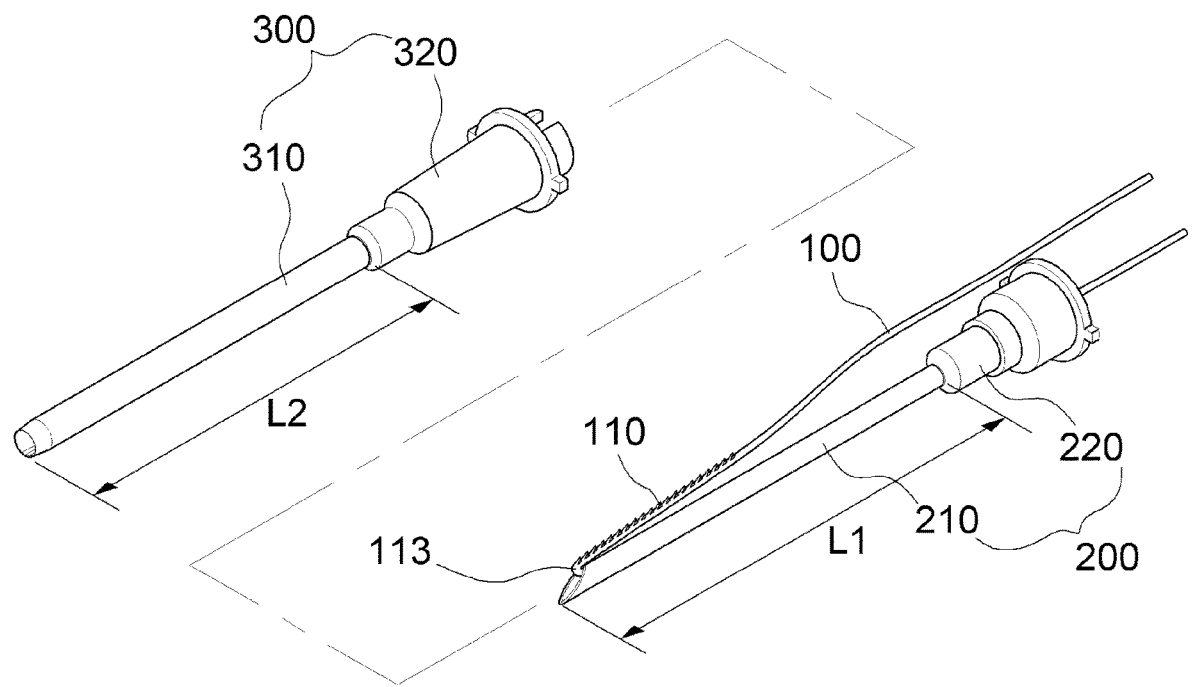
FIG. 3 is a conceptual diagram for a medical thread insertion instrument of the present invention.

Referring to FIG. 3, in order to insert the medical thread 100 as described above into the skin and lift the skin, the medical thread insertion instrument including a needle part 200 and a tube part 300 may be used.

Referring to FIG. 3, the needle part 200 has a predetermined length L1, and includes a needle 210 having a cavity into which the medical thread 100 may be inserted. In addition, a needle guider 220 coupled to one end of a side of the needle 210 may be included.

The needle 210 keeps a cylindrical shape having a cavity therein, so that the medical thread 100 may be inserted thereinto. The needle 210 may be made of a material such as medical stainless, titanium, magnesium, etc. Various exemplary embodiments of a shape-to-structure of the end part of the needle 210 will be described in a fourth exemplary embodiment with reference to FIGS. 3 and 10.

Figure 8A:
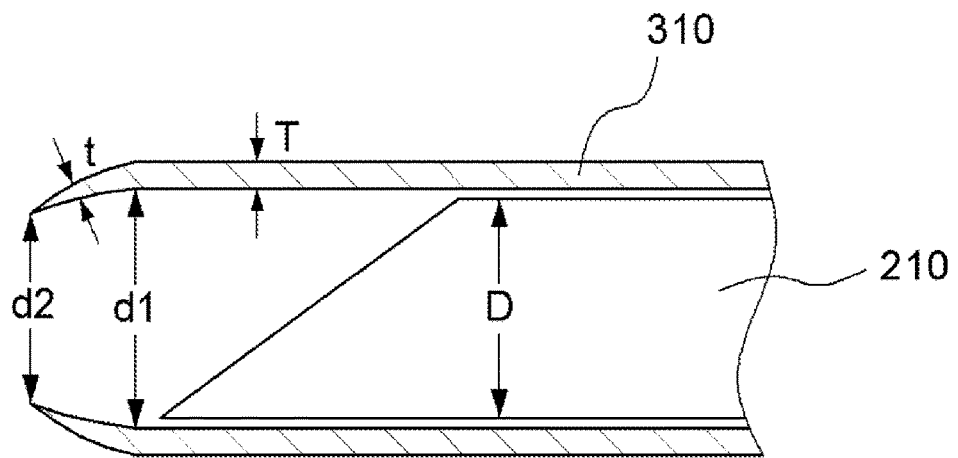
FIGS. 8A and 8B are conceptual diagrams for an exemplary embodiment of the medical thread insertion instrument according to the present invention.
Figure 8B:
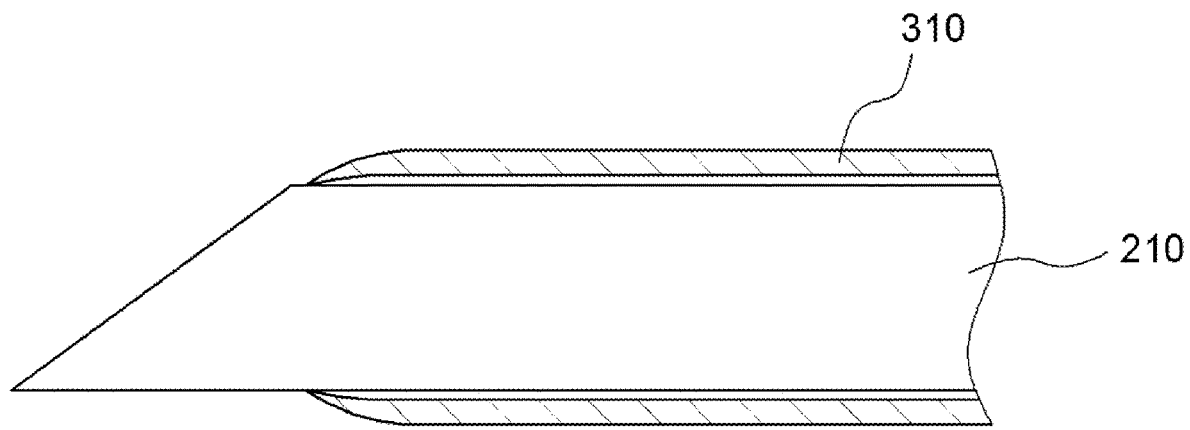

Referring to FIG. 3, the tube part 300 has a predetermined length L2, and may include a tube 310 having a cavity into which the needle 210 may be inserted and a tube guider 320 coupled to an end of the tube 310. The tube 310 is extendedly formed to have a predetermined length and is formed in a cylindrical shape having both sides open. The tube 310 may be made of soft plastic material. Alternately, the tube 310 may be made of medical silicone for human body. Referring to FIGS. 8A and 8B, it is preferable that the inner diameter length d1 of the tube 310 is maintained to be equal to or greater than the outer diameter length D of the needle 210 of the needle part 200 to be described later. This will be described in a second exemplary embodiment.

Referring to FIGS. 5A to 5C, the tube guider 320 is formed on the other side of the tube 310, and a support protrusion 321 may be protrudingly formed on one side of the tube guider 320 facing the needle part 200. A connection part 400 is inserted into or supported by the support protrusion 321, whereby the connection part 400 may be firmly fixed thereto. This will be described in a first exemplary embodiment.

As shown in FIG. 3, about half of the medical thread 100 is inserted into the inner side of the needle 210, and the rest of the medical thread is disposed on the outer side of the needle 210. The needle part 200 into which a part of the medical thread 100 is inserted is inserted into the inner side of the tube 310 of the tube part 300. When the needle 210 in which the medical thread 100 is embedded is inserted into the tube 310, the medical thread 100 exposed to outside of the needle 210 is to be disposed between the inner circumferential surface of the tube 310 and the outer circumferential surface of the needle 210.

After being inserted into the skin, until the needle part 200 is removed, it is preferable that a bent part 113 of the medical thread 100 inserted into the needle 210, or the barb 110 of the medical thread 100 is not exposed toward the outer side of the tube 310. This is to prevent contamination that may be caused by the medical thread 100 being exposed to the outside, and to facilitate correction of a needle when the needle is inserted into a wrong position.

The following exemplary embodiments may be exemplary embodiments independent to each other. It is noted that the exemplary embodiments may be mixed or added to be implemented according to user requirements. Accordingly, overlapped descriptions are refrained from being described as much as possible.

The exemplary embodiments for the description are as follows.

First Exemplary Embodiment

Figure 4:
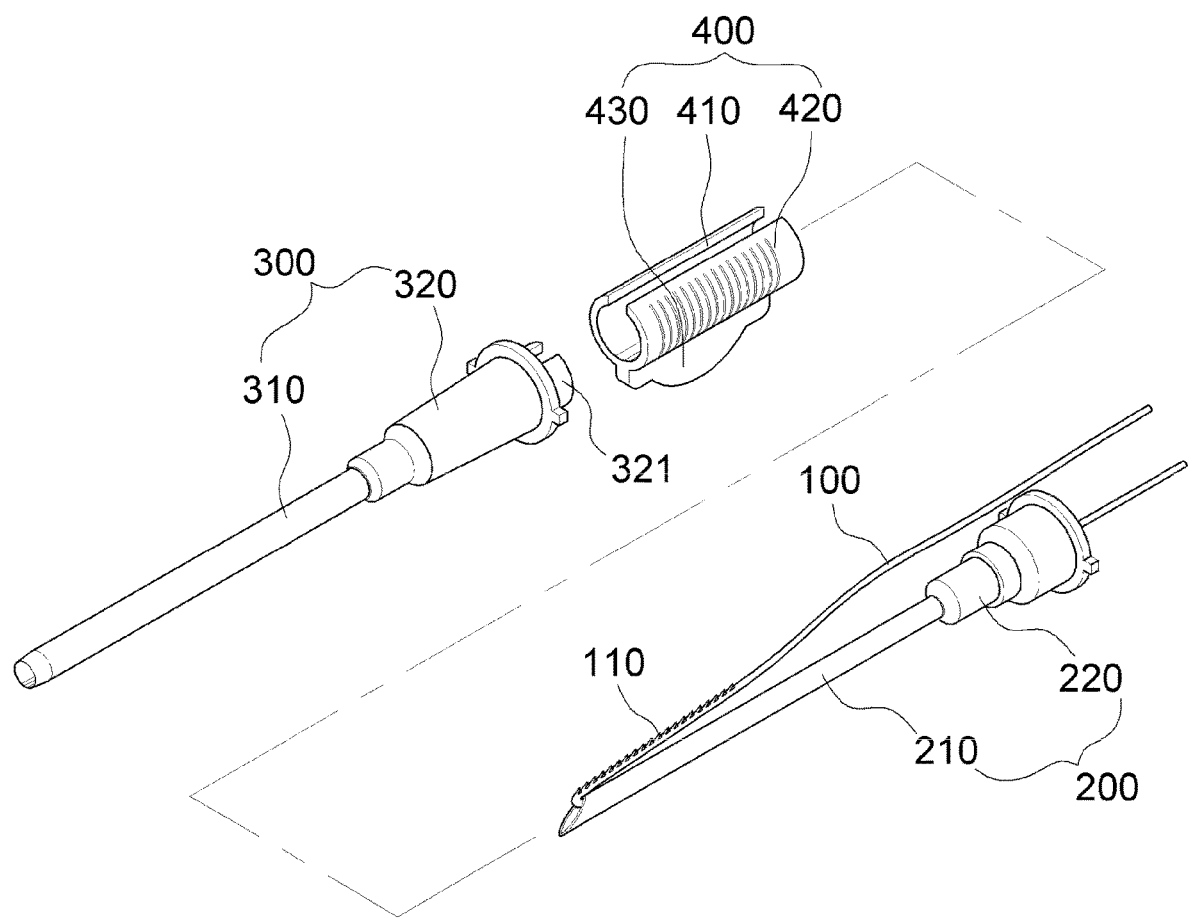
FIG. 4 is another conceptual diagram for the medical thread insertion instrument of the present invention.

Referring to FIG. 4, the medical thread insertion instrument according to the first exemplary embodiment includes a medical thread 100, a needle part 200, a tube part 300, and a connection part 400.

The medical thread 100, the needle part 200, and the tube part 300 are in accordance with the above.

Referring to FIGS. 4 and 5A, as the distal end part of the needle 210 having the medical thread 100 embedded therein protrudes to the end of the tube 310, the connection part 400 allows the needle part 200 and the tube part 300 to be spaced apart at a certain interval so that the barbs 110 of the medical thread 100 are not exposed.

Referring to FIGS. 4 and 5A, the connection part 400 is positioned between the needle part 200 and the tube part 300. The connection part 400 may be fixed to the needle part 200 or the tube part 300. As shown in FIG. 5B, the connection part 400 may be removed during a treatment process. The connection part 400 may be formed in a structure where the user may easily detach the connection part 400 when necessary.

Referring to FIG. 4, the connection part 400 includes a first elastic part 410, a second elastic part 420, and a gripping part 430. The first elastic part 410 has a predetermined length and may be fixed by being coupled to the support protrusion 321 provided on a side of the tube part 300. Being formed with a certain radius of curvature, the first elastic part 410 may be formed to have elasticity.

As shown in FIGS. 4 and 5A, the second elastic part 420 is symmetrical to the first elastic part 410, wherein one side of the second elastic part is integrally connected to one side of the first elastic part 410 and the other end side thereof is formed to be spaced apart from the other end side of the first elastic part 410 by a certain interval, thereby being coupled to and fixed to the support protrusion 321. The second elastic part 420 may also be formed to have a predetermined length, and may enable the needle part 200 and the tube part 300 together with the first elastic part 410 to be spaced apart by certain intervals. The medical thread 100 exposed to the outside of the needle part 200 passes through the gap spaced apart between the first elastic part 410 and the second elastic part 420.

Referring to FIGS. 4 and 5A, the gripping part 430 aims to pull the tube part toward one side of the first elastic part 410 and the second elastic part 420 when the connection part 400 is detached from the tube part 300. The gripping part 430 may be protrudingly formed on the outer side of the first elastic part 410 and the second elastic part 420 so as to be gripped by the user.

Referring to FIGS. 5A to 5C, the medical thread 100, the needle part 200, and the tube part 300 are integrally inserted into the skin tissue S, and then the connection part 400 is detached. Subsequently, when the needle part 200 is pressed with a certain pressure, a part of the end part of the needle 210 having the medical thread 100 embedded therein is further pulled out of the end of the tube 310.

Figure 6A:
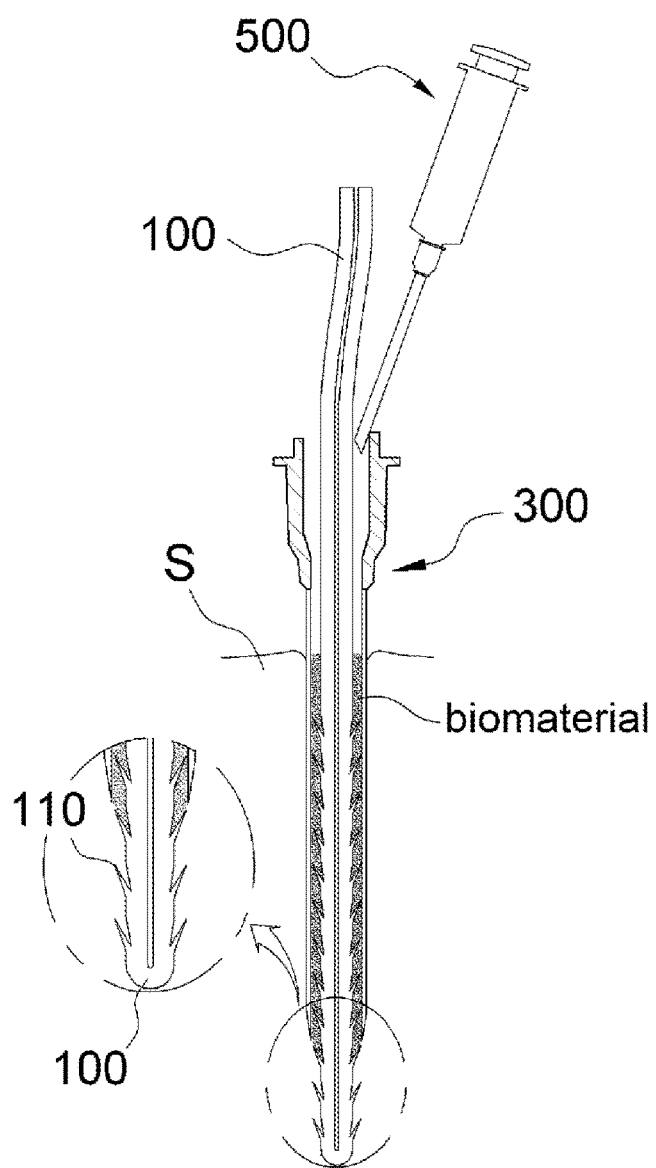
FIGS. 6A and 6B are other conceptual diagrams showing the sequence of insertion of the medical thread by using the medical thread insertion instrument of the present invention.

Referring to FIG. 5C, as much as the medical thread 100 is pulled out, a part thereof exposed to the outside of the tube 310 is made in contact with the skin tissue S. It is preferable that the barbs 110 are formed on the outer circumferential surface of the medical thread 100 in contact therewith. When the needle part 200 is pulled out of the tube part 300, the pulled barbs 110 are caught in the skin tissue S. As shown in FIG. 6A, even when the needle part 200 is removed, since the medical thread 100 does not come out with the needle part 200, the medical thread 100 is positioned in the inner side of the tube 310.

It is assumed that the tube part 300 is inserted into a surgical site other than the desired site of the skin tissue due to medical specialist's carelessness. As shown in FIG. 5C, as long as the connection part 400 is removed, and the needle part 200 is not inserted into the skin, the barbs 110 are not in a state of being caught in the skin tissue S. Accordingly, because the medical thread 100 is not in contact with the skin tissue S, the tube part 300 may be easily pulled out of the skin tissue S, thereby reducing side effects or medical risks. The barb 110 may be prevented from being unable to be pulled out easily due to being caught by the skin tissue S, or may be prevented from damaging the skin tissue S and the barb 110 when the medical thread 100 is forcibly removed.

With reference to the above, a medical thread insertion method will be described.

As shown in FIG. 5A, the tube part 300 into which the needle part 200 having the medical thread 100 embedded therein is inserted is inserted into the skin tissue S. At the time of insertion, a medical specialist may grip the needle part 200 and the tube part 300, or the connection part 400 so as to insert the instrument into the skin.

The connection part 400 maintains an interval between the needle part 200 and the tube part 300. Therefore, as shown in FIG. 5A, the end part of the needle 210 is only slightly protruded to the end part of the tube 310. Alternately, the end part of the needle may be prevented from protruding at all.

As shown in FIG. 5B, the connection part 400 is removed from the tube part 300 after insertion.

As shown in FIG. 5C, the needle part 200 is further pushed into the inside of the skin tissue S by a certain length. The needle 210 of the needle part 200 and the medical thread 100 having a part thereof embedded in the needle are further pushed out from the inner side of the tube 310 toward the skin tissue S side. The barbs 110 formed on the medical thread 100, which is pushed out to the skin tissue S, is in contact with the skin tissue S. Due to the angle of the barb 110 in contact, it is possible to maintain a state fixed to the skin tissue S.

As shown in FIG. 6A, the needle part 200 is pulled out. By the barbs 110 in contact with the skin tissue S, the medical thread 100 does not come out together with the needle part 200. The medical thread 100 is placed inside the tube part 300.

As shown in FIG. 6A, after removing the needle part 200, a biomaterial may be injected. The biomaterial may be injected into the inner side of the skin through a separate tool 500. The biomaterial is a biocompatible material and may be corresponded to materials such as chitosan, polyethylene, PTFT (Polytetrafluoroethyelene), poly(D,L-lactic-co-glycolic acid), polylactic acid, polyglycolic acid, polycaprolactone, polyvalerolactone, polyhydroxybutyrate, polyhydroxyvalerate, and a material made of these copolymers. In addition, the biomaterial may be composed of PBS (Phosphate Buffered Saline), collagen, hyaluronic acid, human cells, cell culture solution, and a mixture thereof to increase the effect of smooth injection and tissue reconstruction.

Figure 6B:
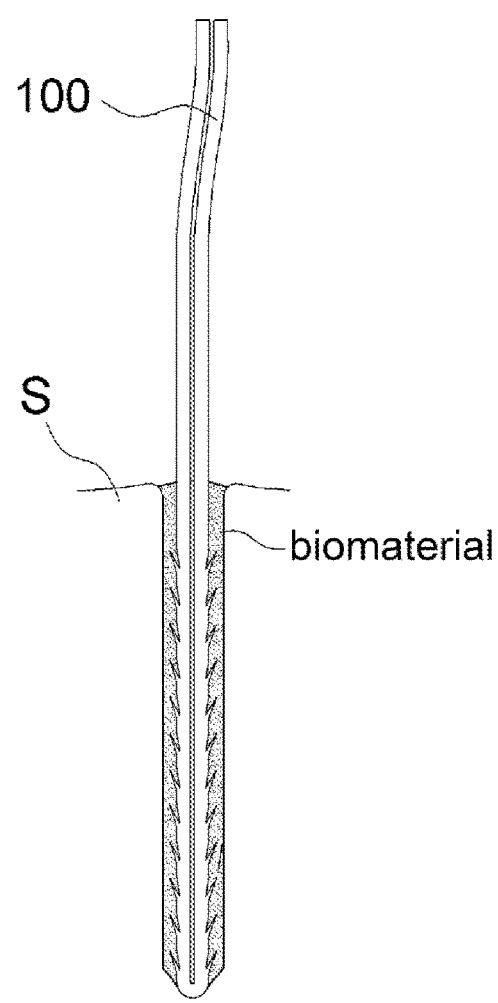
Figure 7:
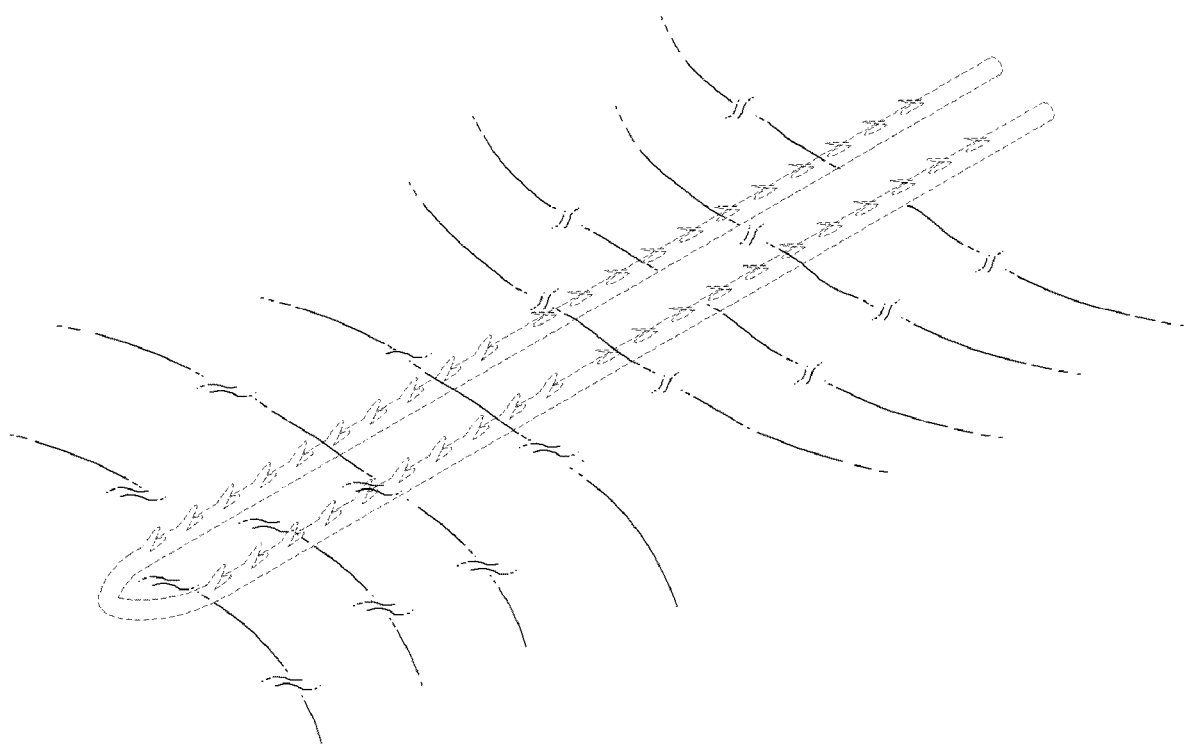
FIG. 7 is a conceptual diagram showing the skin pulled out after inserting the medical thread according to the present invention into the skin tissue.

As shown in FIG. 6B, the tube part 300 is removed. The tube part 300 is pulled out of the skin tissue S so that only the medical thread 100 is placed within the skin tissue S.

Thereafter, the medical thread 100 exposed on the skin surface is pulled to a side. The medical thread 100 may be pulled out in various directions depending on the purpose of the treatment.

In the medical thread of the present invention according to this configuration, the treatment may be rapidly performed by inserting the needle part 200, the medical thread 100, and the tube part 300 into the skin tissue S simultaneously. In addition, by maximally reducing a phenomenon of mutual contact between the barb 110 and the skin tissue S, there is an advantage of preventing a phenomenon from occurring, in which the barb 110 is damaged when the medical thread 100 is inserted into the skin tissue S.

In addition, in the present invention, when removing the needle 210 inserted into the skin tissue S by inserting a part of the medical thread 100 into the skin tissue S by a certain depth, the medical thread 100 may be prevented from being pulled out together with the needle 210 and the engraftment rate between the medical thread 100 and the skin tissue S may be improved by injecting biomaterials.

Second Exemplary Embodiment

Before being inserted into the skin tissue S, the medical thread 100 partially inserted into the needle 210 is prevented from being exposed to the distal end part of the tube 310 as much as possible.

As shown in FIGS. 8A and 8B, the thickness may be tapered toward the end part of the tube 310 (T>t). This is to facilitate insertion into the skin. Meanwhile, the inner diameter of the tube 310 may also be reduced (d1>d2). The inner diameter d2 of the end part side of the tube 310 is preferably smaller than the outer diameter D of the needle 210.

Since the outer diameter D of the needle is larger than the inner diameter d2 of the end part side of the tube 310, it is difficult for the needle 210 having the medical thread embedded therein to be naturally exposed to the tube 310.

As described above, the tube 310 may be made of soft plastic material or medical silicone for human body. For this reason, after being inserted into the skin as shown in FIGS. 8A and 8B, when applying pressure to the end part side of the needle part 200, the distal end part of the tube 310 opens, the needle 210 is exposed toward the outside of the tube 310, and similar to that shown in FIG. 5C, the barbs 110 formed on the medical thread 100 may be exposed to the skin tissue S. Thereafter, the needle part 200 and the tube part 300 are removed in sequence. Various medical purposes such as lifting of the skin may be applicable by utilizing the medical thread 100 which is left behind in the skin tissue S.

Third Exemplary Embodiment

Figure 9A:
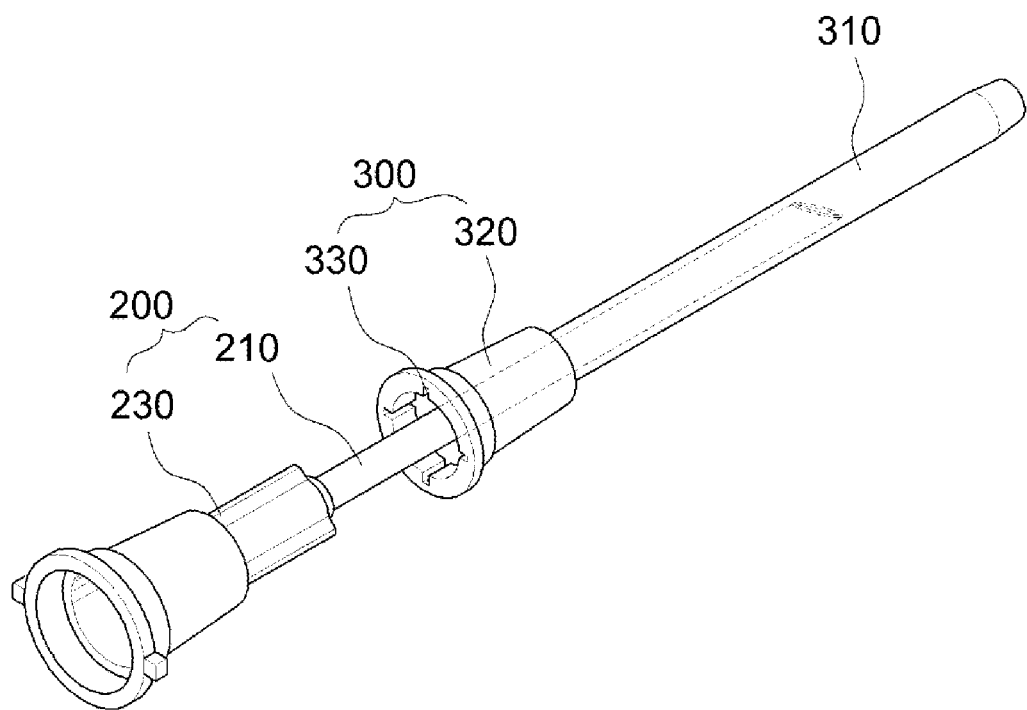
FIGS. 9A to 9C are conceptual diagrams for another exemplary embodiment of the medical thread insertion instrument according to the present invention.
Figure 9B:
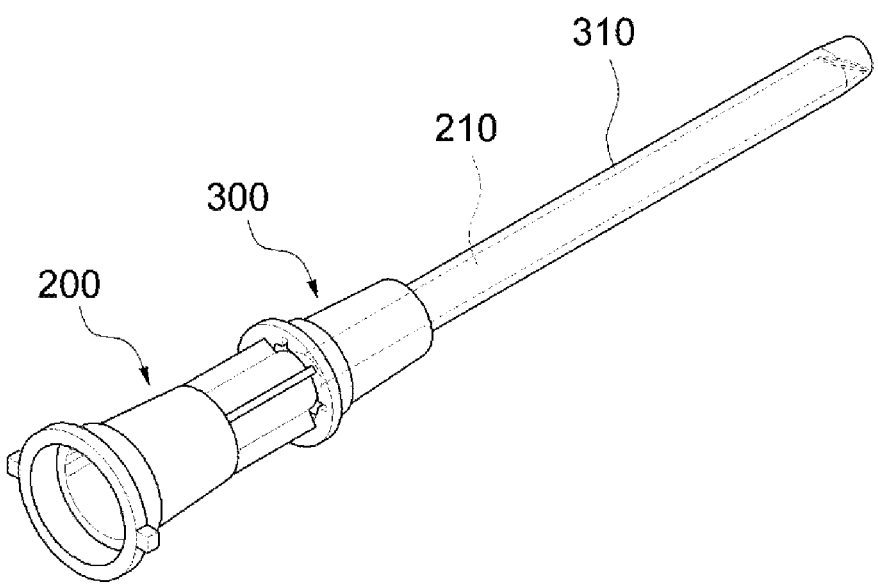
Figure 9C:
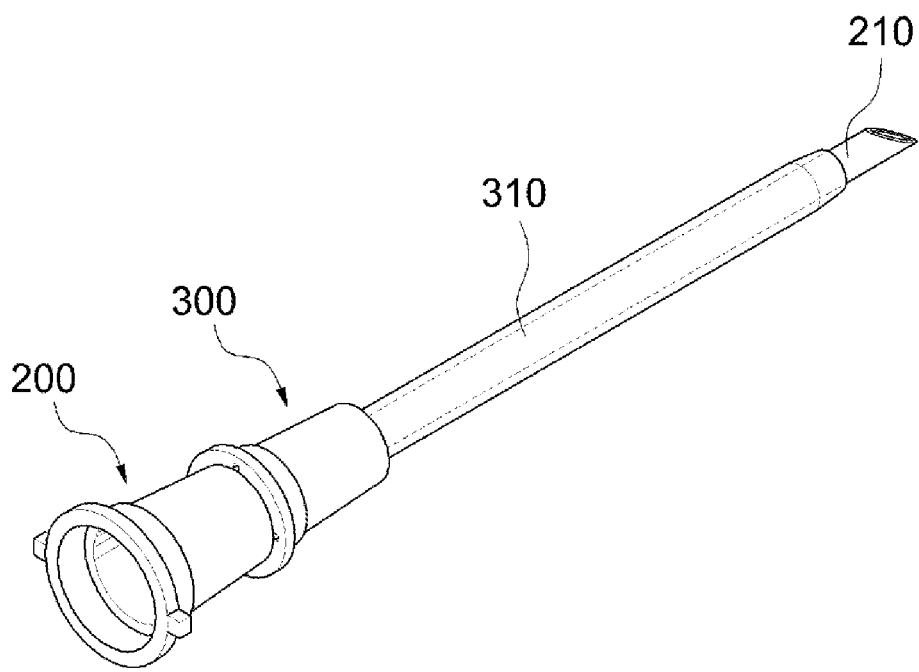

As shown in FIGS. 9A to 9C, a groove or a protrusion 230 on the outer circumferential surface side of the needle guider 200 of the needle part 200 may be formed in the longitudinal direction. To be corresponded to the groove or the protrusion, a protrusion or a groove 330 may be formed on the inner side of the tube guider 320 of the tube part 300.

Referring to FIGS. 9A and 9B, before the protrusion 230 of the needle guider 200 is inserted into a groove 330 of the tube guider 320, the medical thread 100 embedded in the needle does not protrude toward the outer side of the tube 210.

Referring to FIG. 9C, after inserting into the skin tissue S, when the protrusion 230 of the needle guider 200 is inserted into the groove 330 of the tube guider 320, the end part of the needle and a part of the medical thread will be protruded as much as the inserted length.

Afterward, the needle part 200 and the tube part 300 are removed in sequence. Various medical purposes such as lifting of the skin may be applicable by utilizing the medical thread 100 which is left in the skin tissue S.

Fourth Exemplary Embodiment

It will be described with reference to FIGS. 10A and 10B to prevent the distal end part of the medical thread 100 from being exposed to the distal end part of the tube 310 as much as possible.

Figure 10A:
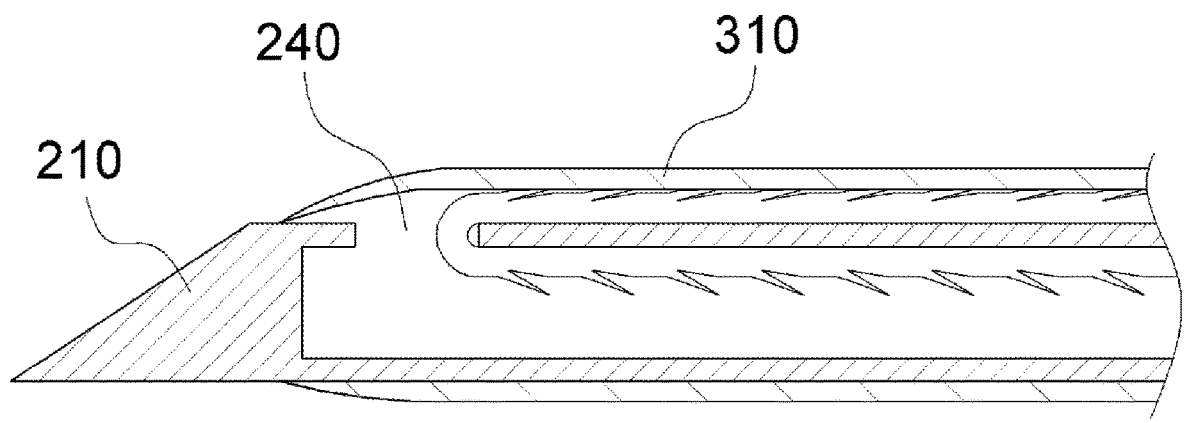
FIGS. 10A and 10B are conceptual diagrams for yet another exemplary embodiment of the medical thread insertion instrument according to the present invention.
Figure 10B:
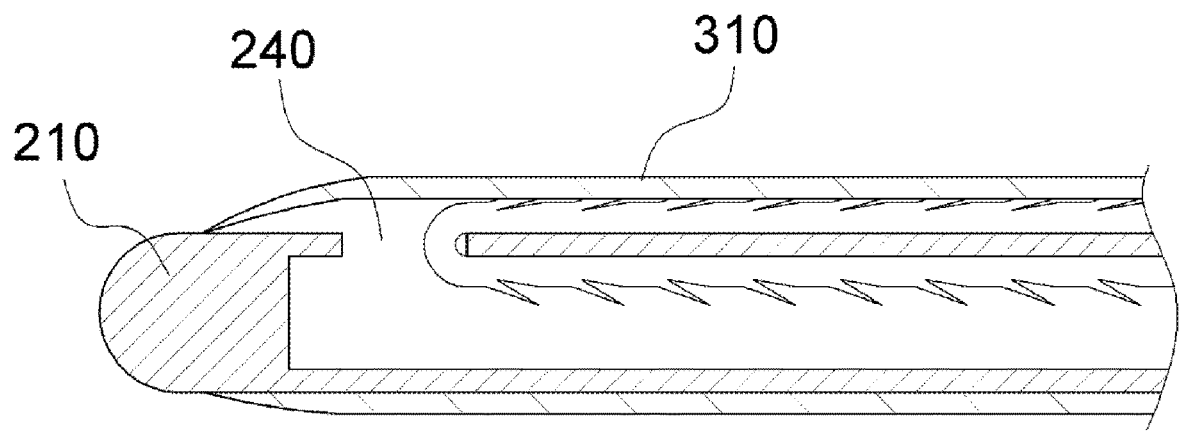

Referring to FIGS. 10A and 10B, the medical thread may be pulled out by closing the distal end part of the needle and drilling a hole 240 positioned on one side of the side surface thereof.

Referring to FIG. 10B, unlike FIG. 10A in which the distal end part of the needle is sharply formed, the end part thereof may be formed in a round shape having a predetermined curvature for the purpose of preventing a safety accident and the like.

As shown in FIGS. 10A and 10B, since the medical thread comes out bent at one side of the end part of the needle, as shown in FIG. 5A, it is possible to prevent the end part of the medical thread from being exposed.

The invention claimed is:

1. A medical thread insertion instrument comprising:
   a medical thread having an outer surface thereof on which barbs are formed;
   a needle part having a cavity therein so that the medical thread is able to be inserted, the needle part including a needle having a predetermined length (L1);
   a tube part having a cavity therein so that the needle is able to be inserted, the tube part configured to be inserted into an inner side of the skin and including a tube having a length (L2) shorter than the predetermined length (L1) of the needle; and
   a connection part for maintaining an interval between the needle and the tube,
   wherein, the tube part into which the needle part and the medical thread are embedded inside the tube part is configured to be inserted into a skin tissue, as the needle is configured to be inserted into the skin tissue, an end part of the needle is able to be protruded toward an outer side of the tube due to a difference in length between the tube and the needle, and
   wherein the connection part is configured to be removed after the insertion into the skin tissue of the tube part into which the needle part and the medical thread are embedded inside the tube part.

2. The medical thread insertion instrument of claim 1, wherein a part of the medical thread on which the barbs are formed is configured to be exposed to the skin tissue toward an outer side of the end part of the protruding needle.

3. The medical thread insertion instrument of claim 2, wherein an inner diameter of a distal end part of the tube through which a distal end part of the needle is pulled out is shorter than a length of the outer diameter of the needle.

4. The medical thread insertion instrument of claim 2, wherein the needle part further comprises a needle guider connected to an end of the needle and having a groove or a protrusion formed on an outer circumferential surface thereof in a longitudinal direction; and
   the tube part further comprises a tube guider connected to an end of the tube and having a protrusion or a groove formed on an inner circumferential surface thereof in a longitudinal direction to correspond to the groove or the protrusion of the needle guider, thus receiving the groove or the protrusion of the needle guider therein.

* * * * *